(12) United States Patent
Silverman et al.

(10) Patent No.: US 9,119,848 B2
(45) Date of Patent: Sep. 1, 2015

(54) MORPHINAN DERIVATIVES FOR THE TREATMENT OF DRUG OVERDOSE

(75) Inventors: Bernard Silverman, Needham, MA (US); Fen-Ni Fu, Northboro, MA (US); Chengyun Guo, McFarland, WI (US)

(73) Assignee: Alkermes Pharma Ireland Limited, Dublin (IE)

( * ) Notice: Subject to any disclaimer, the term of this patent is extended or adjusted under 35 U.S.C. 154(b) by 321 days.

(21) Appl. No.: 12/903,462

(22) Filed: Oct. 13, 2010

(65) Prior Publication Data

US 2011/0136848 A1 Jun. 9, 2011

Related U.S. Application Data

(60) Provisional application No. 61/266,881, filed on Dec. 4, 2009.

(51) Int. Cl.
*A61K 31/485* (2006.01)
*A61K 31/4748* (2006.01)
*C07D 221/22* (2006.01)
*C07D 221/28* (2006.01)

(52) U.S. Cl.
CPC ........... *A61K 31/4748* (2013.01); *A61K 31/485* (2013.01); *C07D 221/22* (2013.01); *C07D 221/28* (2013.01)

(58) Field of Classification Search
CPC ............. A61K 31/4748; A61K 31/485; C07D 221/28; C07D 221/22
USPC ....................................... 514/289; 546/74, 75
See application file for complete search history.

(56) References Cited

U.S. PATENT DOCUMENTS

| | | | |
|---|---|---|---|
| 3,332,950 A | 7/1967 | Blumberg et al. |
| 3,856,795 A | 12/1974 | Yardley |
| 3,957,793 A | 5/1976 | Wentland et al. |
| 4,032,529 A | 6/1977 | Wentland et al. |
| 4,100,228 A | 7/1978 | Dennis et al. |
| RE29,943 E | 3/1979 | Wentland et al. |
| 4,161,597 A | 7/1979 | Olofson et al. |
| 4,176,186 A | 11/1979 | Goldberg et al. |
| 4,205,171 A | 5/1980 | Albertson |
| 4,373,139 A | 2/1983 | Beesley |
| 4,374,139 A | 2/1983 | Mohacsi |
| 4,451,470 A | 5/1984 | Ganti |
| 4,464,378 A | 8/1984 | Hussain |
| 4,473,573 A | 9/1984 | Merz et al. |
| 4,489,079 A | 12/1984 | Guidice et al. |
| 4,649,200 A | 3/1987 | Portoghese et al. |
| 4,929,622 A | 5/1990 | Allen et al. |
| 5,258,386 A | 11/1993 | Newman et al. |
| 5,607,941 A | 3/1997 | Merz et al. |
| 5,847,142 A | 12/1998 | Mudryk et al. |
| 6,365,594 B1 | 4/2002 | Dondio et al. |
| 6,784,187 B2 | 8/2004 | Wentland et al. |
| 6,812,236 B2 | 11/2004 | Gibson et al. |
| 6,887,998 B2 | 5/2005 | Wentland |
| 7,057,035 B2 | 6/2006 | Wentland et al. |
| 7,244,866 B2 | 7/2007 | Carson et al. |
| 7,262,298 B2 | 8/2007 | Wentland |
| 7,265,226 B2 | 9/2007 | Wentland |
| 7,557,119 B2 | 7/2009 | Wentland |
| 7,956,187 B2 | 6/2011 | Wentland |
| 8,026,252 B2 | 9/2011 | Wentland |
| 8,252,929 B2 | 8/2012 | Wentland |
| 8,263,807 B2 | 9/2012 | Wentland |
| 8,354,534 B2 | 1/2013 | Arnelle et al. |
| 8,436,175 B2 | 5/2013 | Wentland |
| 8,642,615 B2 | 2/2014 | Wentland |
| 8,680,112 B2 | 3/2014 | Wentland |
| 8,778,960 B2 | 7/2014 | Deaver et al. |
| 8,802,655 B2 | 8/2014 | Wentland |
| 8,822,488 B2 | 9/2014 | Deaver et al. |
| 2002/0099216 A1 | 7/2002 | Gibson et al. |
| 2003/0181475 A1 | 9/2003 | Kaiko et al. |
| 2003/0187009 A1 | 10/2003 | Wentland |
| 2004/0192715 A1* | 9/2004 | Chasin et al. ................. 514/282 |
| 2004/0254208 A1 | 12/2004 | Weber et al. |
| 2005/0176645 A1 | 8/2005 | Mickle et al. |
| 2005/0182258 A1 | 8/2005 | Schmidhammer et al. |
| 2005/0215799 A1 | 9/2005 | Wentland et al. |
| 2006/0030580 A1 | 2/2006 | Wentland |
| 2006/0063792 A1 | 3/2006 | Dolle et al. |

(Continued)

FOREIGN PATENT DOCUMENTS

| | | |
|---|---|---|
| CA | 2587074 | 5/2006 |
| DE | 2254298 | 5/1974 |

(Continued)

OTHER PUBLICATIONS

Berge et al. "Pharmaceutical Salts"; 1977; Journal of Pharmaceutical Sciences; 66(1): 1-19.*

(Continued)

*Primary Examiner* — Kara R McMillian
(74) *Attorney, Agent, or Firm* — Elmore Patent Law Group, P.C.; Roy P. Issac; Carolyn S. Elmore

(57) ABSTRACT

The instant application relates to morphinan derivatives of Formula I with sustained effectiveness in treating drug toxicity and overdose:

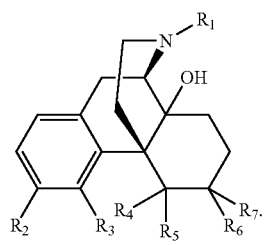

2 Claims, 6 Drawing Sheets

(56) References Cited

U.S. PATENT DOCUMENTS

Figure 1:
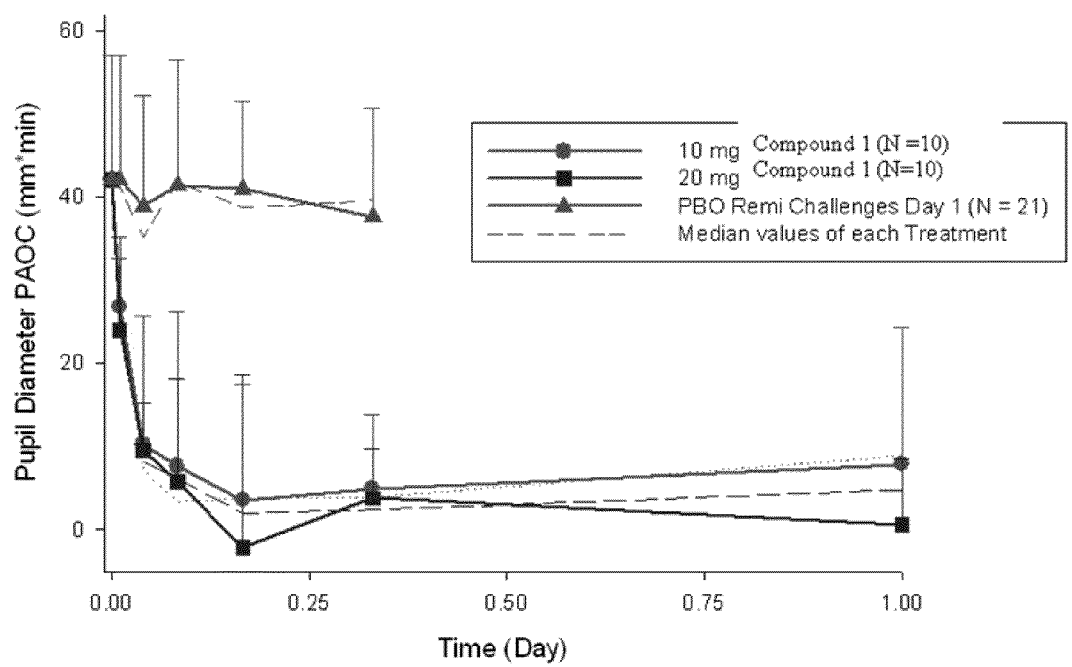

| | | | |
|---|---|---|---|
| 2007/0021457 A1 | 1/2007 | Wentland | |
| 2007/0099947 A1* | 5/2007 | Dean et al. | 514/282 |
| 2007/0238748 A1* | 10/2007 | Wentland | 514/289 |
| 2008/0004324 A1 | 1/2008 | Barak | |
| 2008/0234306 A1 | 9/2008 | Perez et al. | |
| 2009/0053329 A1 | 2/2009 | Peters et al. | |
| 2009/0197905 A1 | 8/2009 | Wentland | |
| 2009/0209569 A1 | 8/2009 | Arnelle et al. | |
| 2009/0247562 A1 | 10/2009 | Wentland | |
| 2009/0311347 A1 | 12/2009 | Oronsky et al. | |
| 2010/0035910 A1 | 2/2010 | Wang et al. | |
| 2010/0048906 A1 | 2/2010 | Wang et al. | |
| 2010/0130512 A1 | 5/2010 | Wentland | |
| 2010/0190817 A1 | 7/2010 | Wentland | |
| 2010/0240691 A1 | 9/2010 | Turncliff et al. | |
| 2011/0136848 A1 | 6/2011 | Silverman | |
| 2012/0010412 A1 | 1/2012 | Duncan | |
| 2013/0231361 A1 | 9/2013 | Wentland | |
| 2013/0281388 A1 | 10/2013 | Deaver et al. | |
| 2014/0303371 A1 | 10/2014 | Duncan | |

FOREIGN PATENT DOCUMENTS

| | | | |
|---|---|---|---|
| EP | 0254120 A2 | 1/1988 | |
| EP | 0632041 | 1/1995 | |
| EP | 1359146 | 11/2003 | |
| ES | 2121553 A1 | 11/1998 | |
| GB | 874217 | 8/1961 | |
| GB | 1340720 | 12/1998 | |
| JP | 40010154 | 5/1965 | |
| WO | 93/11761 | 6/1993 | |
| WO | 97/25331 A1 | 7/1997 | |
| WO | 98/52929 | 11/1998 | |
| WO | 01/12197 A1 | 2/2001 | |
| WO | 01/37785 A2 | 5/2001 | |
| WO | 02/36573 A2 | 5/2002 | |
| WO | 03/101963 A1 | 12/2003 | |
| WO | 2004/005924 A2 | 1/2004 | |
| WO | 2004/007449 A1 | 1/2004 | |
| WO | 2004/045562 A2 | 6/2004 | |
| WO | 2006/052710 A1 | 5/2006 | |
| WO | 2006/096626 A2 | 9/2006 | |
| WO | 2007/014137 A2 | 2/2007 | |
| WO | 2007/067714 A2 | 6/2007 | |
| WO | WO 2007/089934 A2 * | 8/2007 | |
| WO | 2008/144394 A2 | 11/2008 | |
| WO | 2009023567 A1 | 2/2009 | |
| WO | 2010/011619 A1 | 1/2010 | |
| WO | 2010/107457 A1 | 9/2010 | |
| WO | 2010107457 A1 | 9/2010 | |
| WO | 2010/141666 A2 | 12/2010 | |
| WO | 2010141666 A2 | 12/2010 | |
| WO | 2011/119605 A2 | 9/2011 | |
| WO | 2012/018872 A1 | 2/2012 | |
| WO | 2012/088494 A1 | 6/2012 | |

OTHER PUBLICATIONS

U.S. Appl. No. 12/727,784, filed Mar. 2010, Turncliff et al.*
Zaveri N. et al., Small-Molecule Agonists and Antagonists of the Opioid Receptor-Like Receptor (ORL1,NOP): Ligand-Based Analysis of Structural Factors Influencing Intrinsic Activity at NOP, The AAPS Journal, 2005, E345-E352.
Sayre et al., Design and Synthesis of Naltrexone-Derived Affinity Labels with Nonequilibrium Opioid Agonist and Antagonist Activities. Evidence for the Existence of Different μ Receptor Subtypes in Different Tissues, Journal of Medicinal Chemistry, 1984, 1325-1335.
Zhang et al., 10-Ketomorphinan and 3-Substituted-3-desoxymorphinan Analogues as Mixed κ and μ Opioid Ligands: Synthesis and Biological Evaluation of Their Binding Affinity at Opioid Receptors, Journal of Medicinal Chemistry, 2004, 165-174.
Schultz, et al., "Opioids and Cardioprotection," Pharmacology & Therapeutics, vol. 89, 2001, pp. 123-137.
Jarusuraisin, "Opioid Antagonists for Alcohol Dependence Review," The Cochrane Collaboration (Wiley Publishers), 2004, pp. 1-44.
Wentland, et al., 3-Carboxamido analogues of morphine and naltrexone. synthesis and opioid receptor binding properties, Bioorg Med Chem Lett. Jul. 9, 2001;11(13):1717-21.
Wentland, et al., 8-Carboxamidocyclazocine analogues: redefining the structure-activity relationships of 2,6-methano-3-benzazocines, Bioorg Med Chem Lett. Mar. 12, 2001;11(5):623-6.
Bidlack, et al., 8-Carboxamidocyclazocine: a long-acting, novel benzomorphan, J Pharmacol Exp Ther. Jul. 2002;302(1):374-80.
Wentland, et al., 8-Aminocyclazocine analogues: synthesis and structure-activity relationships, Bioorg Med Chem Lett. Jan. 17, 2000;10(2):183-7.
Wentland, et al., Selective protection and functionalization of morphine: synthesis and opioid receptor binding properties of 3-amino-3-desoxymorphine derivatives. J. Med. Chem. Lett. 43: 3558-65 (2000).
Wentland, et al., Redefining the structure-activity relationships of 2,6-methano-3-benzazocines. Part 2: 8-formamidocyclazocine analogues, Bioorg Med Chem Lett. Jun. 2, 2003;13(11):1911-4.
Wentland, et al., Synthesis and opioid receptor binding properties of a highly potent 4-hydroxy analogue of naltrexone, Bioorg Med Chem Lett. Apr. 15, 2005;15(8):2107-10.
Wentland, et al., Redefining the structure-activity relationships of 2,6-methano-3-benzazocines. 4. Opioid receptor binding properties of 8-[N-(4'-phenyl)-phenethyl)carboxamido] analogues of cyclazocine and ethylketocycalzocine, J Med Chem. Sep. 7, 2006;49(18):5635-9.
Vanalstine, et al., Redefining the structure-activity relationships of 2,6-methano-3-benzazocines. 5. Opioid receptor binding properties of N-((4'-phenyl)-phenethyl) analogues of 8-CAC, Bioorg Med Chem Lett. Dec. 7, 2007;17(23):6516-20.
Wentland, et al., Redefining the structure-activity relationships of 2,6-methano-3-benzazocines. Part 6: Opioid receptor binding properties of cyclic variants of 8-carboxamidocyclazocine, Bioorg Med Chem. May 15, 2008;16(10):5653-64.
Wentland, et al., Syntheses and opioid receptor binding properties of carboxamido-substituted opioids, Bioorg Med Chem Lett. Jan. 1, 2009;19(1):203-8.
Wentland, et al., Redefining the structure-activity relationships of 2,6-methano-3-benzazocines. Part 7: syntheses and opioid receptor properties of cyclic variants of cyclazocine. Bioorg Med Chem Lett. Jan. 15, 2009;19(2):365-8.
Wentland, et al., Syntheses of novel high affinity ligands for opioid receptors, Bioorg Med Chem Lett. Apr. 15, 2009;19(8):2289-94.
McCurdy, et al., Investigation of phenolic bioisosterism in opiates: 3-sulfoxamido analogues of naltrexone and oxymorphone, Organic Letters, 2(6) 819-821, 2000.
Danso-Danqarth, R., Synthesis and sigma binding properties of 1'- and 3'-halo- and 1',3'-dihalo-N-normetazocine analogues, J Med Chem. Jul. 21, 1995;38(15):2986-9.
Diaz, et al., SAR and biological evaluation of novel trans-3,4-dimethyl-4-arylpiperidine derivatives as opioid antagonists, Bioorg Med Chem Lett. Sep. 1, 2005;15(17):3844-8.
Ida, The Nonnarcotic Antitussive Drug Dimemorfan: A Review., Clin Ther. Mar.-Apr. 1997;19(2):215-31.
Mohasci, et al., Acylmorphinans. A Novel Class of Potent Analgesic Agents, Journal of Medicinal Chemistry, 1985, 28(9) 1177-80.
Redfern, N., "Dihydrocodeine Overdose Treated with Naloxone Infusion," British Medical Journal, 1983 (287) 751-752.
Clarke, S., et al., "Naloxone in Opioid Poisoning: Walking the Tightrope," Emergency Medicine Journal, 2005 (22)612-616.
Alpharma Pharmaceuticals, ALO-01 (Morphine Sulfate Extended-Release with Sequestered Naltrexone Hydrochloride) Capsules for the Management of Moderate to Severe Pain when a Continuous, Around-the-Clock Opioid Analgesic is Needed for an Extended Period of Time, Meeting of the Anesthetic and Life Support Drugs Advisory Committee, Open Session-Briefing Package, pp. 1-123, Nov. 14, 2008.
Vanalstine, M. Design Synthesis and Evaluation of Novel N-Substituted Derivatives of 8-carboxamidocyclazocine, Thesis, Rensselaer Polytechnic Institute, 2007.

(56) References Cited

OTHER PUBLICATIONS

Saal, Christoph., "Pharmaceutical Salts Optimization of Solubility or Even More?," American Pharmaceutical Review, pp. 1-6, http://www.americanpharmaceuticalreview.com/ downloaded Feb. 7, 2013.
Revia—naltrexone hydrochloride table, film coated, Teva Women's Health Inc., pp. 1-10 (Feb. 2009).
Opioid Overdose, Best Practice, BMJ Evidence Centre, retrieved from the Internet http://bestpractice.bjm.com, Feb. 12, 2013.
Van Dorp, et al., Naloxone Treatment in Opioid Addiction: The risks and benefits, Expert Opin. Drug Saf 6(2): pp. 125-132 (2007).
Richards, K.L., Opioids: Addiction vs. Dependence, HealthCentral, http://www.healthcentral.com/chronic-pain/coping-279488-5.html (Oct. 2013).
Preda, A., Opioid Abuse Treatment & Management, Medscape Drugs, Diseases and Procedures, http://emedicine.medscape.com/article/287790-treatment (Oct. 2013).
OTC Pharm Instructions: Naltrexone Hydrochloride Tablet: http://otc-med-pharm.com/buy_revia_en-us.html?sub=1968 &otc=naltrexo (Oct. 2013).
Beletsky, L., et al., "Physicians' Knowledge of and Willingness to Prescribe Naloxone to Reverse Accidental Opiate Overdose: Challenges and Opportunities," Journal of Urban Health: Bulletin of the New York Academy of Medicine, 84(1): pp. 126-136 (Dec. 2006).
McCurdy, et al., "Investigation of Phenolic Bioisosterism in Opiates: 3-Sulfonamido Analogues of Naltrexone and Oxymorphone," Organic Letters, vol. 2, No. 6, pp. 819-821 (2000).
Davies, et al., "Palladium Catalysed Elaboration of Codeine and Morphine," J. Chem., Soc., Perkin Transl.2, pp. 1413-1420 (2001).
Kubota, et al., "Synthesis and Biological Activity of 3-Substituted . . .," Bior. Med. Chem. Letters., 8, pp. 799-804 (1998).
Wentland, et al., "8-Aminocyclazocine Analogues: Synthesis and Structure . . .," Bior. Med. Chem. Ltrs., 10, pp. 183-187 (2000).
Wentland, et al., "Selective Protection and Functionalization of Morphine," J. Med. Chem., 43, pp. 3558-3565 (2000).
Coop et al, " Opioid Affinity and Selectivity of 4-Hydroxy-3-methoxyindolomorphianan Analogues Related to Naltrindole", J. Med. Chem. 42, 1673-1679 (1999).
Kubota et al. "Palladium-Catalyzed Cyanation of Hindered, Electron-Rich . . . " Tetrahedron Ltrs. 39, 2907-2910 (1998).
Nan et al., Synthesis of 2'-Amino-17-cyclopropylmethyl-6,7-dehydro-3,14-dihydroxy-4,5α-eposy 6,7:4',5'-thiazolomorphinan from Naltrexone[1], J. Heterocyclic Chem. 34, 1195-1203 (1997).
Coop et al, "Direct and Simple Conversion of Codeine to Thebainone-A and Dihydrothebainone", Heterocycles 50, 39-42 (1999).
Neumeyer et al, "Design and Synthesis of Novel Dimeric Morphinan Ligands for and Opioid Receptors", J. Med. Chem. 46, 5162-5170 (2003).
U.S. Appl. No. 14/321,885, filed Jul. 2, 2014 (Wentland).
Alkermes: "Alkermes Initiates Clinical Study of ALKS 5461 for Treatment-Resistant Depression," Retrieved from the internet: URL:http://www.pipelinereview.com/index.php/2011061543028/Neurology-and-Psychiatry/Alkermes-Initiates-Clinical-Study-of-ALKS-5461-for-Treatment-Resistant-Depression.html, retrieved on Mar. 14, 2013 (Jul. 2011 ).
Alkermes: "Strong Results for Alkermes' ALKS 5461 in Major Depressive Disorder," Retrieved from the internet: URL:http//www.thepharmaletter.com/file/109997/strong-results-for-alkermes-ALKS-5461-in-major-depressive-disorder. html, retrieved on Mar. 14, 2013 (Jan. 2012).
Baptista, T., et al., "Naltrexone does not prevent the weight gain and hyperphagia induced by the antipsychotic drug sulpiride in rats," Appetite, 34, pp. 77-86 (2000).
Bell, J., et al., Clinical Guidelines and Procedures for the Use of Naltrexone in the Management of Opioid Dependence, Australia, pp. 1-57 (Aug. 2003).
Belluzzi, J.D., et al., "Enkephalin May Mediate Euphoria and Drive-Reduction Reward," Nature, 266, pp. 556-558 (Apr. 1977).
Bianchetti, et al., "Quaternary Derivatives of Narcotic Antagonists: Stereochemical Requirements at the Chiral Nitrogen for in vitro and in vivo Activity," Life Sciences, 33(Suppl 1), pp. 415-418 (1983).
Bianchi, et al., "Quaternary Narcotic Antagonists' Relative Ability to Prevent Antinociception and Gastrointestinal Transit Inhibition in Morphine-Treated Rats as an Index of Peripheral Selectivity," Life Sciences, 30(22): pp. 1875-1883 (1982).
Bodnar, R., "Preclinic Effects of Opioid Antagonists on Feeding and Appetite," Opiate Receptors and Antagonists: From Bench to Clinic, Dean, Reginald, et al., Human Press pp. 387-406 (Jan. 2009).
Cacchi, et al., "Palladium-Catalyzed Carbonylation of Aryl Triflates," Tetrahedron Ltrs., 27, pp. 3931-3934 (1986).
Cao, et al., "Why is it Challenging to Predict Intestinal Drug Absorption and Oral Bioavailability in Human Using Rat Model," Pharmaceutical Research, 23(8), pp. 1675-1686 (Aug. 2006).
Cone, Ej. et al. Fluorescence Properties of Pseudomorphine and Congeners: Structure-Activity Relationships. Journal of Pharmaceutical Sciences. 1980, vol. 69, p. 254.
Dorwald, F., Zaragoza "Side Reactions in Organic Synthesis," Wiley-VCH, Weinheim p. IX of Preface (2005).
Elman, I., et al., "Food Intake and Reward Mechanisms in Patients with Schizophrenia: Implications for Metabolic Disturbances and Treatment with Second-Generation Antipsychotic Agents," Neuropsychopharmacology 31, pp. 2091-2120 (2006).
Garriock, H.A., et al., "Association of Mu-Opioid Receptor Variants and Response to Citalopram Treatment in Major Depressive Disorder," Am. J. Psychiatry 167(5): pp. 565-573 (May 2010).
Greenway, F., et al., "Effect of Naltrexone Plus Bupropion on Weight Loss in Overweight and Obese Adults (COR-I): a Multicentre, Randomised, Double-Blind, Placebo-Controlled, Phase 3 Trial," The Lancet, Lancet Limited, 376(9741); pp. 595-605 (2010).
Heiner et al., "Efficient Kg-Scale Synthesis of Thrombin Inhibitor CRC 220," Tetrahedron, vol. 51, No. 44, pp. 12047-12068 (1995).
Huidobro-Toro, et al., Comparative Study on the Effect of Morphine and the Opioid-Like Peptides in the Vas Deferens of Rodents: Species and Strain Differences, Evidence for Multiple Opiate Receptors, Life Sciences vol. 28, pp. 1331-1336 (1981).
International Preliminary Examination Report for PCT/US01/45581, date of completion Feb. 5, 2003.
International Search Report and Written Opinion for PCT/US2009/051200, date of mailing Nov. 11, 2009.
International Search Report and Written Opinion from International Application No. PCT/US2008/072632, mailed Dec. 23, 2008.
International Search Report and Written Opinion from International Application No. PCT/US2011/029425, mailed Sep. 16, 2011.
International Search Report and Written Opinion of the International Searching Authority for PCT/US2008/063713, date of mailing May 28, 2009.
International Search report for PCT/US01/45581, date of completion Jul. 30, 2002.
International Search Report from International Application No. PCT/US2005/039911, date of completion Apr. 19, 2006.
International Search Report from International Application No. PCT/US2006/028634, mailed Jan. 26, 2007.
IPRP for International Application No. PCT/US2006/028634, date of issuance Jan. 22, 2008.
Isseroff, R.G., et al., "Regionally Selective Increases in 1-1 Opioid Receptor Density in the Brains of Suicide Victims," Brain Research 530, pp. 312-316 (1990).
Kennedy, S.E., et al., "Dysregulation of Endogenous Opioid Emotion Regulation Circuitry in Major Depression in Women," Arch Gen Psychiatry 63, pp. 1199-1208 (Nov. 2006).
Ko, MC, et al., "Differentiation of kappa opioid agonist-induced antinociception by naltrexone apparent pA2 analysis in rhesus monkeys," J Pharmacol Exp Ther. May 1998;285(2):518-26.
Morera, et al., "A Palladium-Catalyzed Carbonylative Route to Primary Amides," Tetrahedron Ltrs. 39, pp. 2835-2838 (1998).
Nagata, H. et al. A concise route to (-)-morphine. ChemComm. 2001, p. 1094, scheme 2.
Plodkowski Ra, et al., "Bupropion and naltrexone: a review of their use individually and in combination for the treatment of obesity," Expert Opin Pharmacother. Apr. 2009;10(6):1069-81.

(56) References Cited

OTHER PUBLICATIONS

Pub Chem CID 15974736, Created Mar. 14, 2007; Retrieved Jun. 22, 2011 (http://pubchem.ncbi.nlm.nih.gov/summary/summary.cgi?cid= 1597 4 736).

Pub Chem CID 16667612, Created Aug. 16, 2007; Retrieved Sep. 2, 2011 (http://Qubchem.ncbi.nlm.nih.gov/summary/summm:y.cgi?cid= 16667612&loc=ec res).

Pub Chem CID 15586509, Created Feb. 12, 2007; Retrieved Sep. 2, 2011 (http://pubchem.ncbi.nlm.nih.gov/summary/summary.cgi?cid= 15586506&loc=ec res).

Remmers, AE, Medzihradsky F.Resolution of biphasic binding of the opioid antagonist naltrexone in brain membranes. J Neurochem. Oct. 1991;57(4):1265-9.

Rennison, D., et al., Structural Determinants of Opioid Activity in Derivatives of 14-Aminomorphinones: Effects of Changes to the Chain Linking of the C14-Amino Group to the Aryl Ring, Journal of Medicinal Chemistry 49(20): pp. 6104-6110 (2006).

Simpkins, et al., "Evaluation of the Sites of Opioid Influence on Anterior Pituitary Hormone Secretion Using a Quaternary Opiate Antagonist," Neuroendocrinology, 54(4): pp. 384-390 (1991).

Taylor DM, McAskill R. Atypical antipsychotics and weight gain—a systematic review. Acta Psychiatr Scand. Jun. 2000;101(6):416-32.

Tek, C., et al., "Investigating the safety and efficacy of naltrexone for anti-psychotic induced weight gain in severe mental illness: study protocol of a double-blind, randomized, placebo-controlled trial," BMC Psychiatry, 13, p. 176 (2013).

Todtenkopf, M., et al., "In vivo Characterization of Novel, Peripherally-Acting Opioid Antagonists," Society for Neuroscience Abstract Viewer and Itinerary Planner, vol. 38, 38th Annual Meeting of the Society-for-Neuroscience, Nov. 2008.

Varma, et al., "Microwave-Acceelrated Solvent-Free Synthesis of Thioketones," Thiolactones, Thioamides, Thionoesters, and Thioflavonoids, Organic Letters, vol. 1, No. 5, pp. 697-700 (1999).

Wells T. Ghrelin—Defender of fat. Prog Lipid Res. Sep. 2009;48(5):257-74. Epub May 4, 2009.

Wentland, Mark P., et al., "Syntheses and Opioid Receptor Binding Affinities of 8-Amino-2,6-methano-3- benzazocines," Journal of Medicinal Chemistry, 2003, pp. 838-849, vol. 46, No. 5.

Wentland, Mark, et al., "Redefining the Structure-Activity Relationships of 2,6-methano-3-benzazocines. Part 3: 8-Thiocarboxamido and 8-thioformamido Derivatives of Cyclazocine," Bioorg. Med. Chem. Lett., 15(10), pp. 2547-2551 (2005).

Written Opinion of International Application No. PCT/US2005/039911, completed Apr. 19, 2006.

Yamamoto et al., "Buprenorphine Activates 1-1 and Opioid Receptor Like-1 Receptors Simultaneously, but the Analgesic Effect Is Mainly Mediated by 1-1 Receptor Activation in the Rat Formalin Test", Journal of Pharmacology and Experimental Therapeutics, vol. 318, No. 1, pp. 206-213 (2006).

Yuan, C., et al., "Methylnaltrexone Potentiates Body Weight and Fat Reduction with Leptin," Journal of Opioid Management: A Medical Journal of Proper and Adequate Use, Weston Medical Publishing, 5(6): pp. 373-378 (Nov. 2009).

Zhang J, et al., The mu-opioid receptor subtype is required for the anorectic effect of an opioid receptor antagonist. Eur J Pharmacol. Sep. 18, 2006;545(2-3):147-52. Epub Jul. 5, 2006.

Jendralla, et al., "Efficient Kg-Scale Synthesis of Thrombin Inhibitor CRC 220", Tetrahedron vol. 51, No. 44 pp. 12047-12068 (1995).

* cited by examiner

MORPHINAN DERIVATIVES FOR THE TREATMENT OF DRUG OVERDOSE

RELATED APPLICATION(S)

This application claims the benefit of U.S. Provisional Application No. 61/266,881, filed on Dec. 4, 2009. The entire teaching of the above application is incorporated herein by reference.

TECHNICAL FIELD

This invention relates to mophinan compounds useful for the treatment of drug toxicity and overdose, in particular opioid overdose.

BACKGROUND OF THE INVENTION

Opioids are a class of drugs that include both natural and synthetic substances. The natural opioids (referred to as opiates) include opium and morphine. Heroin, the most abused opioid, is synthesized from opium. Other synthetic opioids, commonly prescribed for pain, as cough suppressants, or as anti-diarrhea agents, includes, codeine, oxycodone (OXYCONTIN®), meperidine (DEMEROL®), fentanyl (SUBLIMAZE®), hydromorphone (DILAUDID®), methadone and propoxyphene (DARVON®). Heroin is usually injected, either intravenously or subcutaneously, but can also be smoked or used intranasally. Other opioids are either injected or taken orally.

Opioids, whether used in a clinical or non-clinical environment, are highly addictive and can lead to varying degrees opioid toxicity. Some chronic opioid users known as "addicts" continue abusing the opioid despite significant problems caused by or made worse by the use of opioid. Typically, chronic users become physically dependent on the opioid, as evidenced by tolerance and/or withdrawal. Acute users experience opioid intoxication, wherein the user uses a sufficient amount of an opioid to get a "high". These acute users do not experience typical withdrawal symptoms upon elimination of the opioid, however, may experience overdose symptoms (e.g., opioid-induced coma) when too much of an opioid is taken.

Traditionally there are several forms of opioid detoxification programs targeting users with various degrees of opioid tolerance. Typical treatment regimes allow for complete elimination of the opioid from the user's body and prevent the user from reestablishing a dependence on the opioid. Opioid receptor antagonists are one form of treatment effective at reversing the clinical features of opioid toxicity. Opioid receptor antagonist functions by completely binding to the same receptors as the opioid. The opioid receptor antagonist displaces the opioid while having the added advantage of having no addictive potential because of its inability to activate opioid receptors. This approach has the promising effect of reducing the pharmacodynamic effects (e.g. "high") of the opioid user at a very rapid rate while allowing for the opioid agonist to be eliminated from the body. However, the very rapid removal rate of the opioid may result in exaggerated withdrawal symptoms for addicts with tolerance to the opioid.

An opioid antagonist, naloxone (NARCAN®), is often administered to reverse the effects of opioid intoxication or overdose. The drawback to this treatment is that the duration of action of some opioids may exceed that of a single naloxone administration. The pharmacodynamic actions of naloxone last for a briefer period than all but the most short acting opioids. Clarke, S F J et al., Emergency Medicine Journal, 2005 (22) 612-616. Clarke notes that, "although the elimination half life of naloxone is similar to that of morphine (60-90 minutes) it is redistributed away from the brain more rapidly. Consequently, the patients may become renarcotised and suffer harm if they self discharge from medical care early. Clinicians are clearly walking a tightrope between precipitating AWS (acute withdrawal syndrome) and avoiding renarcotisation." Clarke at 612. Therefore, continued surveillance is needed which is often achieved by hospitalization. Furthermore, in patients with renal and hepatic failures require large doses of naloxone over long periods. Maintaining therapeutically effective naloxone concentration is a challenge. Redfern, N., British Medical Journal, 1983 (287) 751-752. As such, new therapeutics for the treatment of drug overdose/toxicity that are effective for a longer period is needed.

SUMMARY OF THE INVENTION

The present invention relates to the unexpected discovery that certain carboxamide substituted morphinans are useful for the treatment of drug overdose and symptoms of drug overdose, in particular opioid overdose. The carboxamide substituted morphinans are effective in treating drug overdose for longer periods in comparison to naloxone, for example 24 to 48 hours. Another aspect of the invention is the use of carboxamide substituted morphinans in combination or in conjunction with naloxone for the treatment of drug overdose, in particular opioid overdose. In yet another aspect of the invention is the treatment of opioid overdose in opioid experienced non-dependent patients.

The present invention relates to the treatment of drug overdose by the administration of compounds of Formula I:

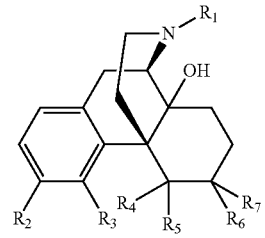

Formula I or a pharmaceutically acceptable salt, ester or prodrug thereof, wherein;

$R_1$ is —$(CH_2)_n$-c-$C_3H_5$, —$(CH_2)_n$-c-$C_4H_7$, —$(CH_2)_n$-c-$C_5H_9$, —$(CH_2)_n$—CH=$CH_2$ or —$(CH_2)_n$—CH=C$(CH_3)_2$ wherein n is independently 0, 1, 2 or 3;

$R_2$ is —$CONH_2$ or —$CSNH_2$;

$R_3$ and $R_4$ are independently H, —OH or together $R_3$ and $R_4$ form an —O— or —S— group;

$R_5$ is H or $C_1$-$C_8$ alkyl; and $R_6$ and $R_7$ are independently H, —OH, $OCH_3$ or together $R_6$ and $R_7$ form a =O or =$CH_2$ group.

Compounds of the instant application are useful in the treatment of drug overdose resulting from opioid drugs such as codeine, heroin, hydromorphone, methadone, propoxyphene oxycodone, oxymorphone, hydrocodone or and morphine.

DETAILED DESCRIPTION OF THE INVENTION

FIG. 1: Pupilometry measures on day 1.

Figure 2:
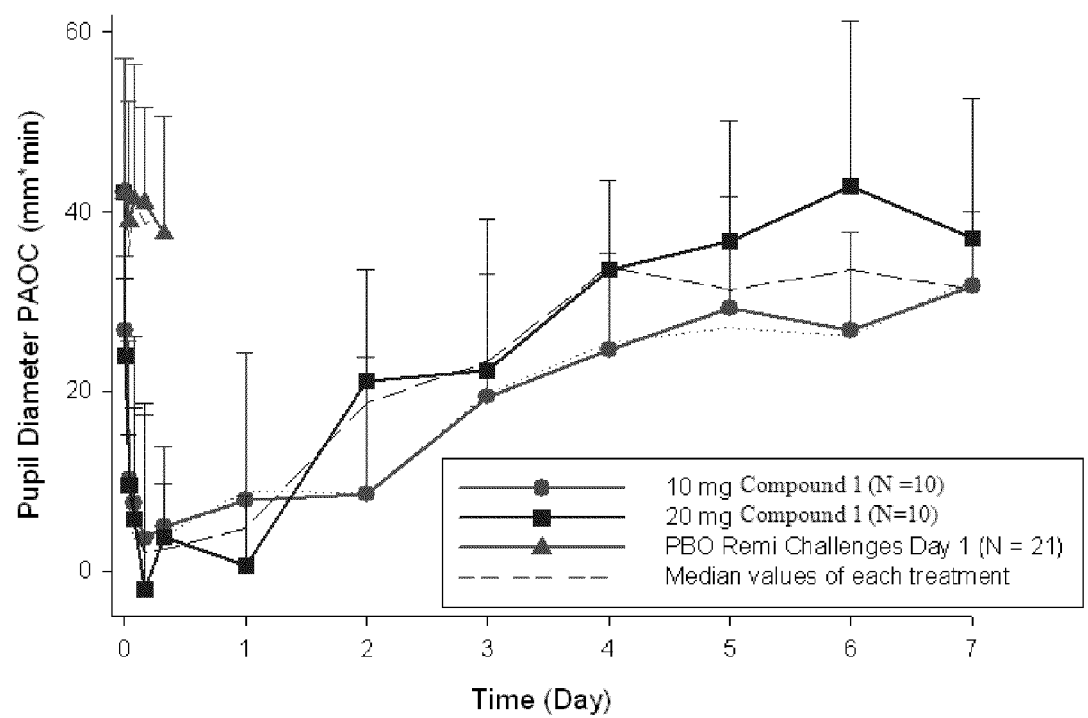

FIG. 2: Pupilometry measures for days 1 to 7.

Figure 3:
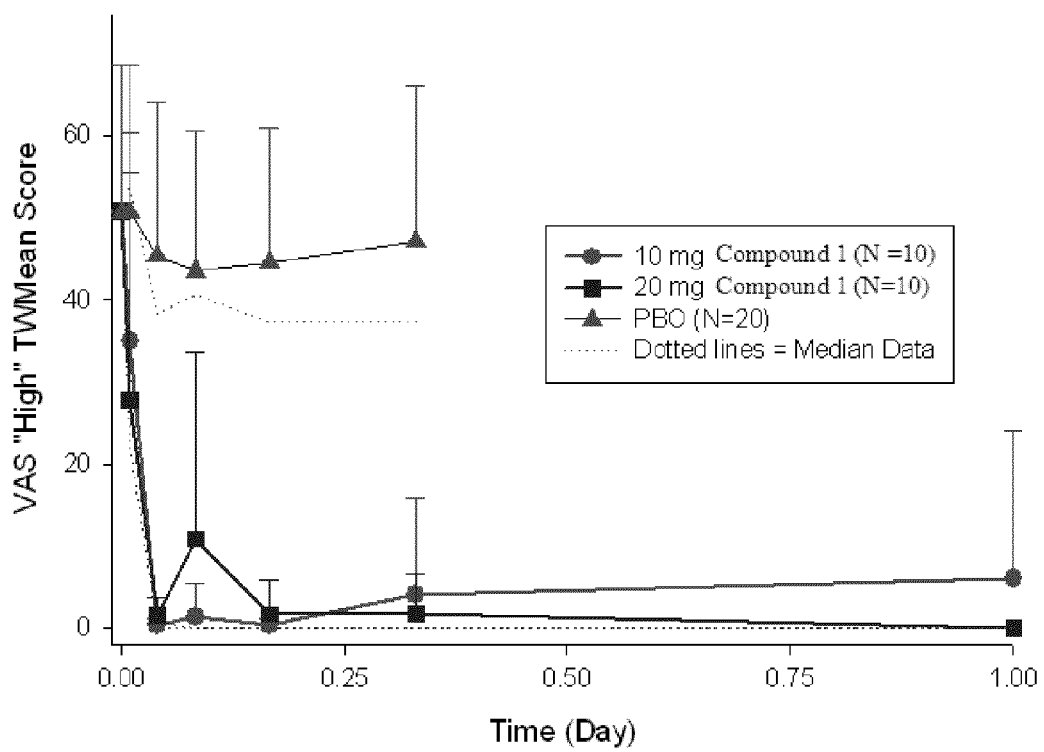

FIG. 3: Visual analog scale (VAS) score for "High" on day 1.

Figure 4:
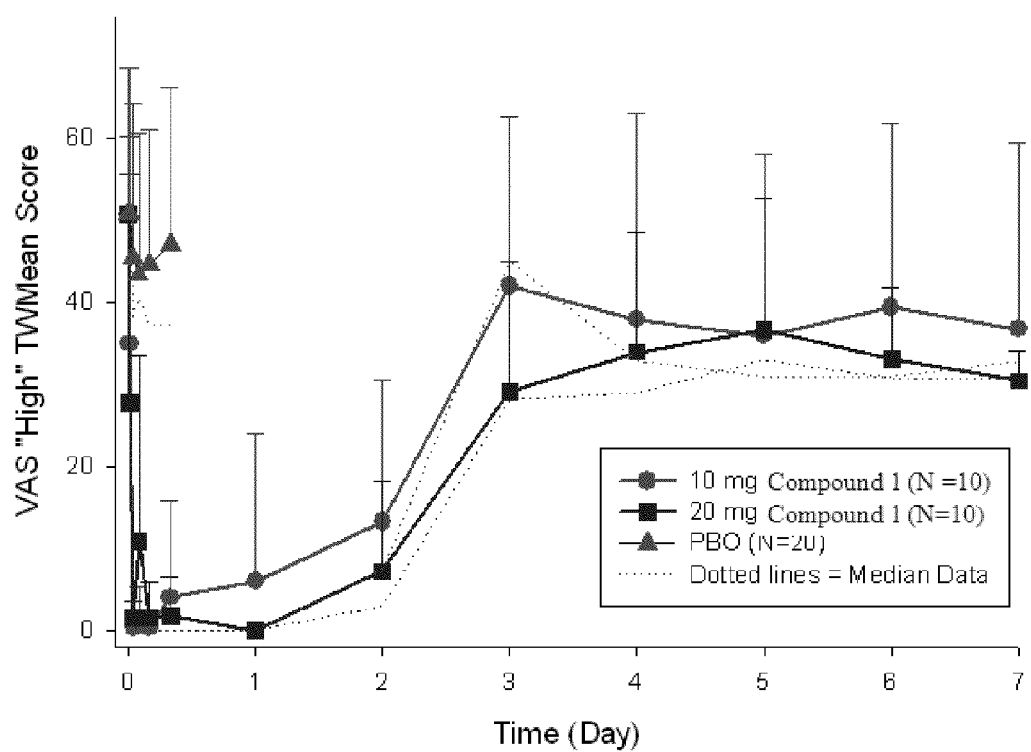

FIG. 4: VAS score for "High" for days 1-7.

Figure 5:
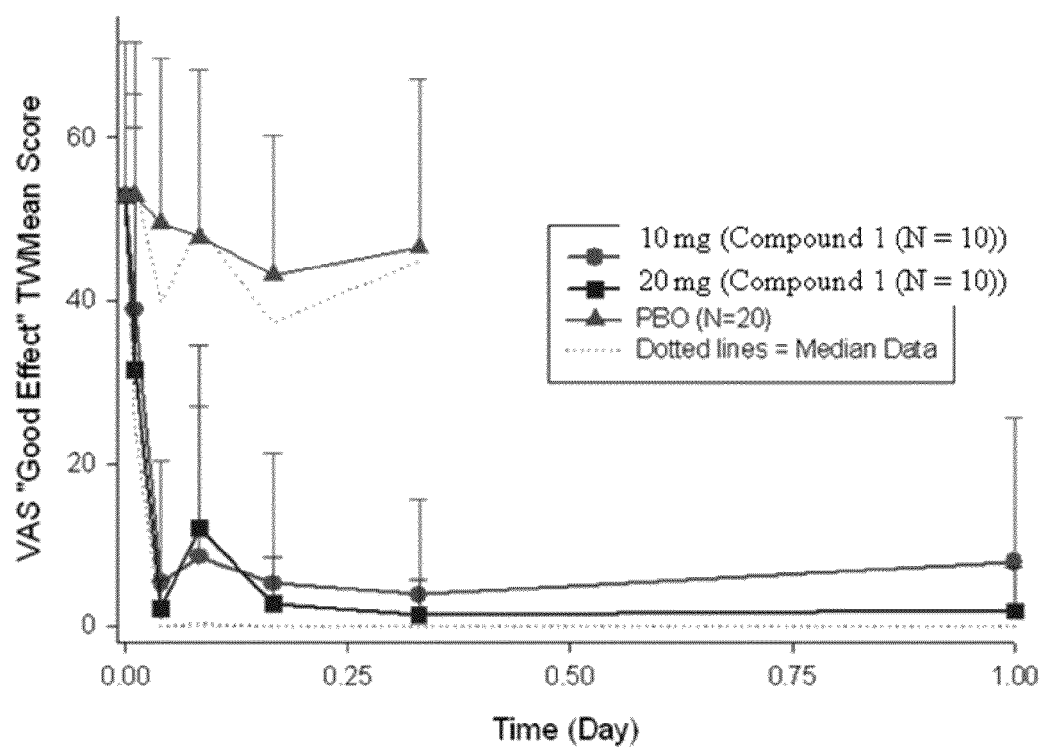

FIG. 5: VAS score for "Good effect" o days 1.

Figure 6:
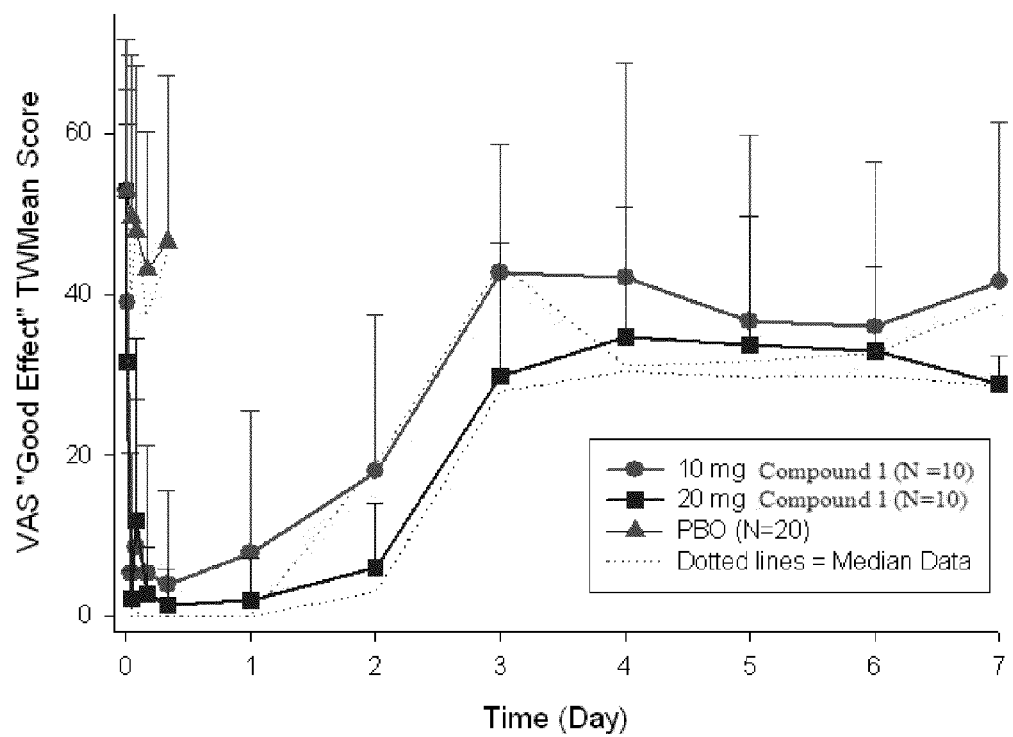

FIG. 6: VAS score for "Good effect" for days 1-7.

The present invention relates to the use of carboxamide substituted morphinans of Formula I for the treatment of drug toxicity or overdose. The present invention relates to the unexpected discovery that compounds of Formula I exhibit sustained efficacy for treating patients suffering from drug toxicity or overdose. The compounds of Formula I can be used as a single dose or once daily dose for the treatment of opioid toxicity or overdose.

Compounds of the instant application are useful in the treatment of drug overdose resulting from opioid drugs such as alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, mixtures of any of the foregoing.

The compounds of Formula I are particularly useful for the treatment of subjects that are opioid experienced non-dependent patients suffering from opioid toxicity or overdose. For example, those patients who have used opioid drugs in the past and have not developed tolerance or dependence to the opioid drugs can be treated for opioid toxicity or overdose. The prolonged period of effectiveness of compounds of Formula I is beneficial for unmonitored treatment of opioid overdose or toxicity. For example, the effectiveness from a single dose administration can last from about 30 minute to over 48 hours. A time period for effectiveness can be over 1 hour; preferably over 2 hours; preferably over 3 hours; preferably over 4 hours; more preferably over 8 hours; more preferably over 24 hours and even more preferably over 48 hours. In a preferred embodiment, the effectiveness of a single dose administration can last between about 1 hour and about 96 hours. In some embodiments, the effectiveness can last between about 24 hours and about 96 hours. In some embodiments, the effectiveness can last between about 24 hours and about 72 hours.

Compounds of the instant invention can be obtained by conversion from the phenolic hydroxyl of benzomorphan to a carboxamide moiety. Phenolic hydroxyls of benzomorphan and morphinan derivatives can be chemically converted to carboxamides by a simple, flexible and convenient route described in U.S. Pat. Nos. 6,784,187, 7,262,298 and 7,057,035, and in U.S. Patent Application Publication No. US 2007/0021457 A1, which are all incorporated herein by reference.

In one aspect the invention relates to the treatment of drug overdose by oral or intravenous or intramuscular administration of compounds of Formula I:

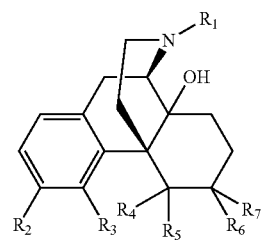

Formula I or a pharmaceutically acceptable salt, ester or prodrug thereof, wherein;

$R_1$ is $-(CH_2)_n$-c-$C_3H_5$, $-(CH_2)_n$-c-$C_4H_7$, $-(CH_2)_n$-c-$C_5H_9$, $-(CH_2)_n-CH=CH_2$ or $-(CH_2)_n-CH=C(CH_3)_2$ wherein n is independently 0, 1, 2 or 3;

$R_2$ is $-CONH_2$ or $-CSNH_2$;

$R_3$ and $R_4$ are independently H, $-OH$ or together $R_3$ and $R_4$ form an $-O-$ or $-S-$ group;

$R_5$ is H or $C_1$-$C_8$ alkyl; and $R_6$ and $R_7$ are independently H, $-OH$, $OCH_3$ or together $R_6$ and $R_7$ form a $=O$ or $=CH_2$ group.

Representative compounds according to Formula I include the following:

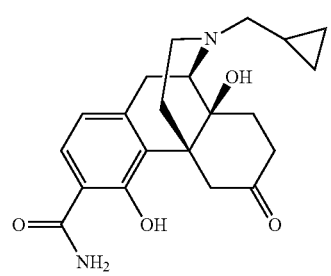

1

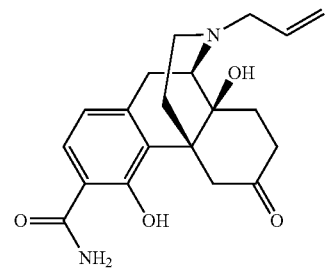

2

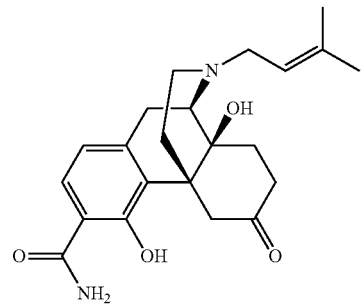

3

5
-continued

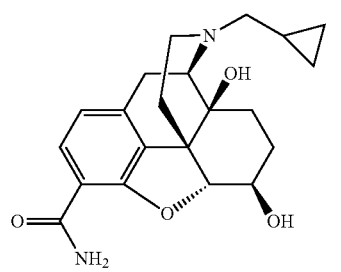
4

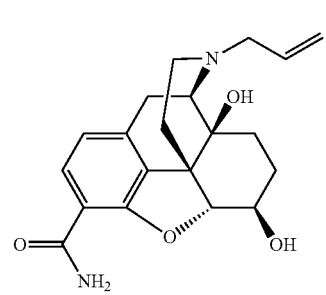
5

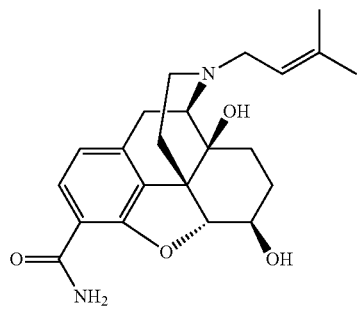
6

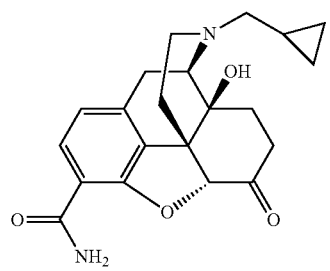
7

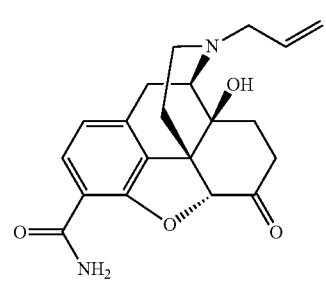
8

6
-continued

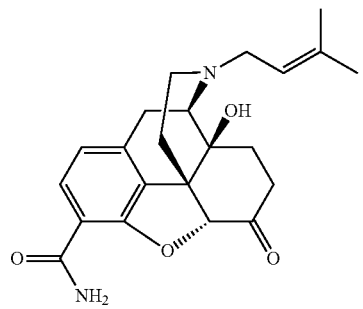
9

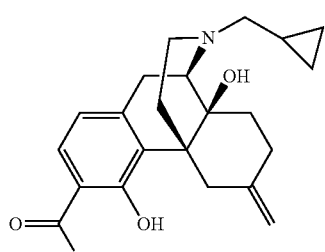
10

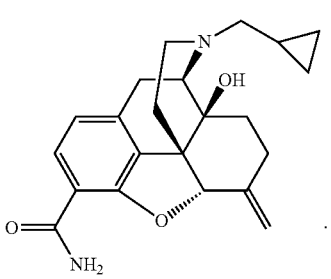
11

A more preferred compound is the maleate salt of Compound 1 having the formula:

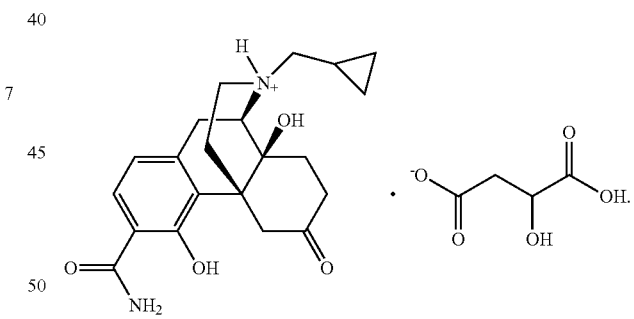

Definitions

Listed below are definitions of various terms used to describe this invention. These definitions apply to the terms as they are used throughout this specification and claims, unless otherwise limited in specific instances, either individually or as part of a larger group.

The term "side effect" refers to adverse effects produced by a drug, especially on a tissue or organ system. In the case of opioids, the term "side effect" may refer to such conditions as, for example, respiratory depression, acute sedation, constipation, opioid-induced bowel dysfunction, nausea and/or vomiting.

The term "$C_1$-$C_8$ alkyl," as used herein, refer to saturated, straight- or branched-chain hydrocarbon radicals containing from one to six, or from one to eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described herein, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, and as would be understood by the person of skill in the art, the recitation of "a compound," unless expressly further limited, is intended to include salts, solvates, esters, prodrugs and inclusion complexes of that compound.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

The term "opioid drugs" as described herein include, but is not limited to the following drugs; alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propoxyphene, sufentanil, tilidine, tramadol, mixtures of any of the foregoing.

The term "opioid toxicity" refers to the effects of opioid drugs that are toxic to the subject, resulting in effects such as moderate to severe ventilatory depression, hypoxia, loss of consciousness, decreased respiratory rate, decreased respiratory depth, apnea, hypoxia, delirium, hypotension, bradycardia, decreased body temperature, urinary retention and pupil miosis. The opioid toxicity can be assessed by performing a central nervous system review by assessing for confusion, altered mental state, excessive drowsiness, lethargy, stupor, slurred speech (new onset), hypoventilation, shortness of breath, apnea, hypoxia, and/or hypercarbia; and/or cardiac review by assessing for bradycardia, hypotension, and/or shock.

The term "opioid experienced" refers to subjects that have taken an opioid at least once prior to the instance for which treatment is sought.

The term "non-dependent" refers to subjects that have taken an opioid at least once without becoming dependent prior to the instance for which treatment is sought.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, carbonate, citrate, cyclopentanepropionate, digluconate, dodecylsulfate, ethanesulfonate, ethanedisulfonate, ethylenediaminetetraacetate (edetate), formate, fumarate, glucoheptonate, glutamate, glycerophosphate, gluconate, hemisulfate, heptanoate, hexanoate, hydroiodide, 2-hydroxy-ethanesulfonate, hydroxynaphthoate, isethionate, lactobionate, lactate, laurate, lauryl sulfate, malate, maleate, malonate, mandelate, methanesulfonate, mucate, 2-naphthalenesulfonate, nicotinate, nitrate, oleate, oxalate, palmitate, pamoate, pantothenate, pectinate, persulfate, 3-phenylpropionate, phosphate, picrate, pivalate, polygalacturonate, propionate, salicylate, stearate, succinate, sulfate, tannate, tartrate, teoclate, thiocyanate, p-toluenesulfonate, undecanoate, valerate salts, and the like. Representative alkali or alkaline earth metal salts include sodium, lithium, potassium, calcium, magnesium, aluminum, zinc and the like. As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates. Further pharmaceutically acceptable salts include, when appropriate, nontoxic ammonium cations and carboxylate, sulfonate and phosphonate anions attached to alkyl having from 1 to 20 carbon atoms.

The term "monitored treatment" refers to treatment administered in a clinic, hospital, doctors office or in a setting where a medical professional is present.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms can be made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides).

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Preferred suitable daily oral dosages for the compounds of the inventions described herein are on the order of about 1.5 mg to about 20 mg. Dosing schedules may be adjusted to provide the optimal therapeutic response. For example, administration can be one to three times daily for a time course of one day to several days, weeks, months, and even years, and may even be for the life of the patient. Practically speaking, a unit dose of any given composition of the invention or active agent can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration twice daily, once daily, every other day, three times weekly, twice weekly, once weekly, twice monthly, once monthly, and so forth. Unit dose preparations can contain a compound of Formula I in the range of about 1.5 to about 30 mg. Preferably, a unit dose form can contain about 1.5 to about 20 mg of a compound of Formula I, while even more preferably a unit dose can have about 1.5 to about 10 mg of a compound of Formula I.

Pharmaceutical kits useful in treating opioid overdose or toxicity with compounds of Formula I of the invention, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL® two-part container (available from Abbott Labs, Chicago, Ill.), as desired. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

The compounds of Formula I according to the present invention may be synthesized employing methods taught, for example, in U.S. Pat. Nos. 5,250,542, 5,434,171, 5,159,081, 4,176,186, 6,365,594, 6,784,187 and 5,270,328, the disclosures of which are hereby incorporated herein by reference in their entireties. Synthetic methodology for indolylmorphinans is described in Jones et al., Journal of Medicinal Chemistry, 1998, 41, 4911. Synthetic methodology for pyridomorphinans is described in Ananthan et al., Bioorganic & Medicinal Chemistry Letters, 13, 2003, 529-532. The optically active and commercially available Naltrexone was employed as starting material in the synthesis of the present compounds may be prepared by the general procedure taught in U.S. Pat. No. 3,332,950, the disclosure of which is hereby incorporated herein by reference in its entireties. Compounds 1a and 1b were synthesized from their corresponding phenols using methodology described in the following references: U.S. Pat. No. 6,784,187; Wentland et al. Bioorganic & Medicinal Chemistry Letters, 2001, 11, 623; Wentland et al., Bioorganic & Medicinal Chemistry Letters, 2001, 11, 1717, Wentland et al., Bioorganic & Medicinal Chemistry Letters, 2005, 15, 2107.

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

A single-center, randomized, single-blind, placebo-controlled study was conducted in 24 healthy, non-dependent, opioid experienced subjects. Placebo (Quinine solution (0.01% w/v)) was administered on Day 1. Compound-1 (10 or 20 mg) was administered on Day 2. Five remifentanyl (REMI) and 2 saline infusion challenges were administered on Day 1 and Day 2. Daily REMI and saline challenges were administered on Days 3-9. At each challenge repeated pharmacodynamic (PD) evaluations were conducted up to 25 minutes post-infusion including pupil diameter. The onset of blockade of remifentanil-induced miosis by Compound-1 was analyzed by comparing PD parameters of maximum pupil constriction (MPC) and pupillometry area over the curve ($PAOC_{0-25\ minutes}$) derived for each challenge infusion time-point on Day 1 (placebo) vs. the corresponding time-points on Day 2. (FIGS. 1 and 2).

Visual analog scales (VAS) scoring for "high" and "good effects" etc., were assessed immediately following pupillometry measurements. Each VAS test cycle lasted approximately 1 minute and included questions associated with each VAS measure. Subjects rated their current perceptions of their subjective state and of the effects of the challenge infusion. (FIGS. 3-6).

The degree, onset, and duration of blockade were determined by statistical comparison of pupil miosis and VAS score at each challenge. REMI produced significant PD effects on Day 1 (p<0.001 vs saline). Compound-1 (10 and 20 mg) blocked pupil miosis induced by REMI within 1 hour (hr) and 0.25 hr, respectively. Blockade persisted for at least 24 hours (p=0.54 vs saline). Blockade of subjective effects of "Drug Liking" persisted for at least 48 hours (p=0.31 vs saline). Compound-1 concentrations greater than 15 ng/mL were sufficient for full blockade. Partial blockade of physiologic and subjective effects persisted through 4 days post-dose, even after more than 99% of Compound-1 had been eliminated ($t_{1/2}$=7 hr).

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

Along with the patients set out above, one opioid dependent, opioid experienced subject was given Compound-1 (10 mg) after REMI challenge. The patient experienced severe drug withdrawal 2 minutes post-dosing with 10 mg of Compound-1 on Day 2. Withdrawal symptoms included nausea, chills, headache, diarrhea, back pain, muscle cramps, and vomiting. These were assessed as a collective and determined to be symptoms of opiate withdrawal. The subject was discontinued from the study prior to receiving the 0.25 hour remifentanil challenge infusion.

The results of the study, particularly the rapid onset and extended effectiveness, in combination with the withdrawal symptoms observed in the opioid dependent patient points to the usefulness of Compound-1 for the treatment of opioid overdose and toxicity.

Example 2

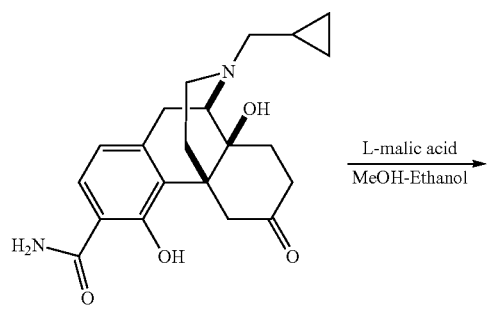

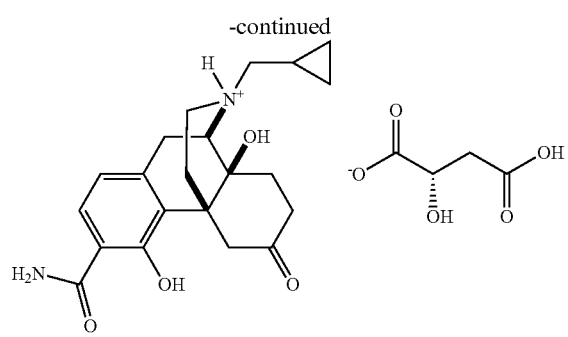

To a jacketed reactor under an inert atmosphere, Compound-1 (80 g) was added. Methanol (250 mL) was added to the reactor, followed by ethanol (250 mL). The contents of the reactor was warmed to approximately 65° C. An ethanolic solution of malic acid (34.5 g of malic acid in 100 mL of ethanol) was added to the reactor at 60-65° C. After stirring at elevated temperature the reactor content was slowly cooled to room temperature. The solids were isolated by filtration, followed by washing of the wet cake with several volumes of methanol:ethanol (40:60) solution. The solids were dried in a vacuum oven until constant weight was reached.

NMR (300 MHz, DMSO-$d_6$): 14.37, 0.9H, s; 12.39, 1.3H, br; 8.41, 1.2H, s; 7.93, 1.2H, s; 7.66, 1.1H, d; 6.65, 1.2H, d; 6.29-4.83, 1.6H, m, 4.04, 1.2H, m; 3.87, 1.2H, d; 3.48, 1.2H, d; 3.10, 2.1H, m; 2.90-2.73, 2.9H, m; 2.72-2.48, 4.5H, m; 2.37, 1.1H, dd; 2.13, 2H, m; 1.96, 1.1H, m; 1.80, 1.9H, m; 1.59, 1H, d; 0.97, 1H, m; 0.57, 2H, m; 0.27, 2H, m.

While this invention has been particularly shown and described with references to preferred embodiments thereof, it will be understood by those skilled in the art that various changes in form and details may be made therein without departing from the scope of the invention encompassed by the appended claims.

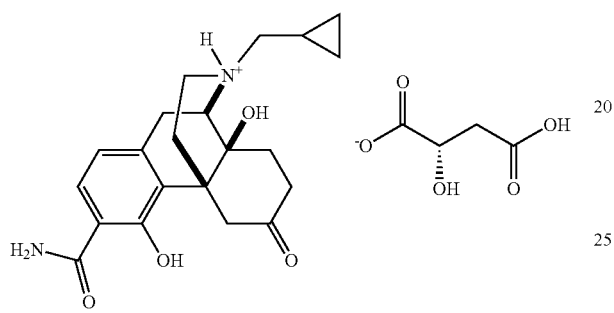

What is claimed is:

1. A method of treating opioid toxicity or overdose in a subject in need thereof comprising administrating L-malate salt of Compound-1 having the formula:

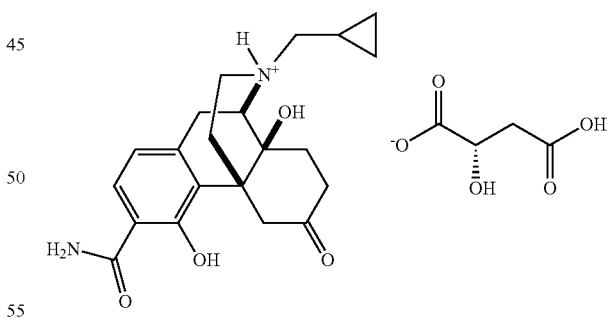

wherein said opioid toxicity or overdose is resulting from opioid administration to a non-dependent patient;

wherein said opioid toxicity or overdose results from an opioid drug selected from alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, mixtures thereof 2. An L-malate salt of compound-1 having the formula: